(12) United States Patent
Lee et al.

(10) Patent No.: US 7,635,795 B2
(45) Date of Patent: Dec. 22, 2009

(54) SIMULATED MOVING BED ADSORPTIVE SEPARATION PROCESS COMPRISING PREPARATION OF FEED BY USING SINGLE ADSORPTION CHAMBER AND DEVICE USED THEREIN

(75) Inventors: Jin-Suk Lee, Chungcheongnam (KR); Nam-Cheol Shin, Chungcheongnam (KR)

(73) Assignee: Samsung Total Petrochemicals Co., Ltd., Daesan-Up, Seosan-Shi, Chungcheongnam Province (KR)

( * ) Notice: Subject to any disclaimer, the term of this patent is extended or adjusted under 35 U.S.C. 154(b) by 594 days.

(21) Appl. No.: 11/613,600

(22) Filed: Dec. 20, 2006

(65) Prior Publication Data

US 2007/0149841 A1 Jun. 28, 2007

(30) Foreign Application Priority Data

Dec. 26, 2005 (KR) .................. 10-2005-0129457

(51) Int. Cl.
*C07C 7/135* (2006.01)
(52) U.S. Cl. .................. 585/828; 585/822; 585/826; 422/129; 422/141; 422/154; 422/155
(58) Field of Classification Search .................. None
See application file for complete search history.

(56) References Cited

U.S. PATENT DOCUMENTS

| 3,239,455 A | * | 3/1966 | Lickus et al. ............... 208/212 |
| 4,326,092 A | | 4/1982 | Neuzil |
| 5,382,747 A | | 1/1995 | Kulprathipanja |
| 6,063,978 A | * | 5/2000 | Hotier et al. ................ 585/814 |
| 6,399,846 B1 | * | 6/2002 | MacPherson et al. ....... 585/814 |
| 6,896,811 B2 | * | 5/2005 | Heikkila et al. ............. 210/659 |
| 2008/0149565 A1 | * | 6/2008 | Lee et al. .................... 210/663 |

FOREIGN PATENT DOCUMENTS

KR     20010051842      6/2001

* cited by examiner

*Primary Examiner*—Tam M Nguyen
(74) *Attorney, Agent, or Firm*—Barlow, Josephs & Holmes, Ltd.

(57) ABSTRACT

Provided is a process for adsorptive separation of p-xylene from an aromatic hydrocarbon mixture comprising other isomers of xylene, and a device used therein. More specifically, the present invention provides a separation process employing simulated moving bed (SMB) adsorptive chromatography, characterized by pretreating a fluid mixture, i.e. the feed, by using single adsorption chamber so as to raise the concentration of a component to be separated, and then carrying out the simulated moving bed adsorptive separation, thereby improving productivity, and a device used therein.

8 Claims, 3 Drawing Sheets

SIMULATED MOVING BED ADSORPTIVE SEPARATION PROCESS COMPRISING PREPARATION OF FEED BY USING SINGLE ADSORPTION CHAMBER AND DEVICE USED THEREIN

FIELD OF THE INVENTION

The present invention relates to a separation process for adsorptive separation of p-xylene from an aromatic hydrocarbon mixture comprising other types of xylene isomers, and a device used therein, more specifically to a separation process employing simulated moving bed (SMB) adsorptive chromatography, characterized by pretreating a fluid mixture, i.e. the feed, so as to raise the concentration of a component to be separated, and then carrying out the simulated moving bed adsorptive separation, thereby improving productivity, and a device used therein.

BACKGROUND OF THE INVENTION

Conventional batch chromatography is a separation process which uses a principle of adsorption mechanism. Since it is suitably used for separation with high purity, assays carried out in a laboratory and the like, it is widely used in a separation or purification process of biosynthetic compounds with high purity, fine chemical compounds, food additives and the like. However, such separation processes using batch chromatography have some problems such that it requires a large amount of solvent used as a mobile phase; separation of a component is hardly achieved when the component to be separated has a similar adsorption property; and it is not appropriately used for separation in massive amount and continuous separation.

In order to solve these problems, a true moving bed (TMB) adsorptive separation process has been suggested in literatures such as Korean laid-open patent application No. 2001-51842 and the like. The TMB process introduces the concept of a counter current flow which has been efficiently used in various processes such as heat exchange and extraction, in which a flow which is counter to the flow direction of the mobile phase is applied to the stationery phase, thus when a mixed solution intended to be separated is fed into a column, a component which has stronger adsorption tendency to the stationary phase comes out of the column along with the flow of the stationery phase, and another component which has lower adsorption tendency to the stationary phase comes out of the column along the flow of the mobile phase. Therefore, this process is advantageous in that it is possible to obtain pure substance as long as two components can be separated at each end point of the concentration distribution curves of the two components, although they have not so much different separability. In the meantime, it also has disadvantages such that the amount of a filling material should be increased as compared to the conventional fixed type separation process, and work in normal state is hardly achieved owing to the friction and leakage of the filling material.

For overcoming these problems of the TMB process, a simulated moving bed (SMB) adsorptive separation process has been developed. The SMB process solves the problems related to the flow of a stationery phase in the TMB process, with the simulation of the counterflow of the solid phase by filling and fixing the adsorbent that is a stationary phase into a column and stepwise moving the ports between columns at a certain time interval. Currently, the SMB process is applied to a separating and purifying process of p-xylene from aromatic hydrocarbon mixtures, a separation process of ethyl benzene, a separation process of chiral compounds and the like. One representative SMB process among SMB processes which are commercially practiced is disclosed in U.S. Pat. Nos. 4,326,092 and 5,382,747 applied by UOP LLC, normally referred as "Parex process".

Parex process is comprised of one or two long adsorption chambers connected in series, wherein the adsorbent chamber is divided into a number of adsorbent beds, normally 12 beds per adsorbent chamber. In a simulated moving bed adsorptive separation process like Parex process, the flow of a stationery phase is not practically realized. Instead, positions of inlet and outlet ports for desorbent, extract, fluid mixture (feed), raffinate and cleaning liquid are moved in the direction of the flow of a mobile phase at a certain time interval of rotary valve rotation, so as to move the columns in the counter direction relative to the flow direction of the mobile phase, with each port as the center, wherein the time interval of the rotary valve rotation is referred as switching time. As such, the virtual flow of the stationery phase can be made to simulate the counterflow to the flow of the mobile phase. The adsorbent used as a stationery phase is filled into the bed.

In Parex process, although each position of ports for desorbent, extract, fluid feed mixture and raffinate cannot be continuously moved, similar effects can be obtained by providing a multiple access line and periodically switching each flow to adjacent line by using a rotary valve at a given time interval of switching time. During the process, a material with lower adsorption in the fluid feed mixture injected through a feed inlet port, comes out though a raffinate outlet port along the mobile phase, and a material with higher adsorption in the fluid feed mixture is adsorbed to each adsorbent bed of the adsorbent chamber. As the column relatively moves at a certain switching time, the adsorbed material can be recovered through the extract outlet port after a certain time elapse.

However, the conventional Parex process for the production of p-xylene has a limit in improving productivity, since the concentration of p-xylene in the feed mixture is not high enough. In order to overcome the setback, a method called selective toluene disproportionation, STDP, has been developed, and in case of a process using a conventional crystallizer, a hybrid method comprising pretreatment in an adsorption tower for increasing the production has also been developed. However, these methods still have limitation in increasing the concentration of p-xylene in the feed mixture for final separation to the desired extent.

SUMMARY OF THE INVENTION

With a view to solve the above-described problems of prior arts, the object of the present invention is to provide a simulated moving bed adsorptive separation process which can increase the concentration of a component intended to be separated in a fluid feed mixture in a SMB adsorptive separation, by pretreating the fluid feed mixture in a single adsorption chamber before carrying out the SMB adsorptive separation, thereby increasing productivity, and a device used therein.

Figure 1:
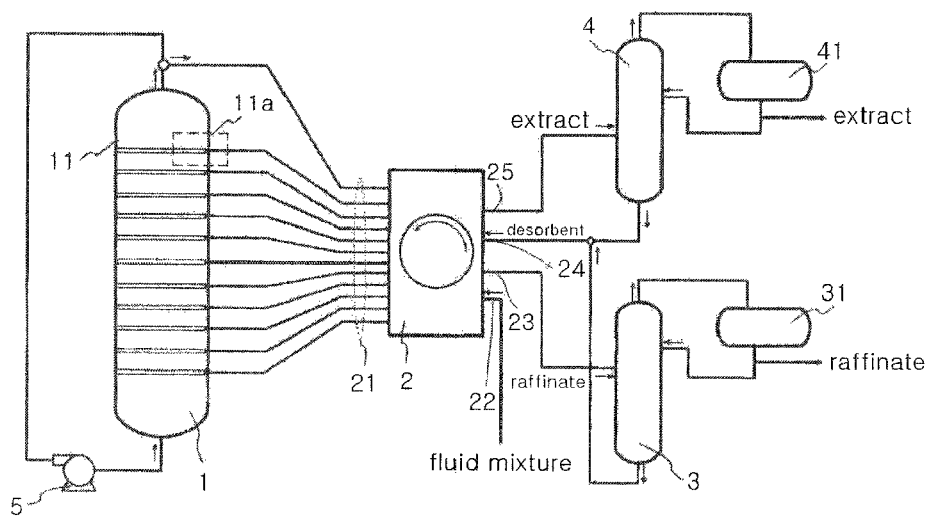
FIG. 1 is a schematic view illustrating a device used in a simulated moving bed (SMB) adsorptive separation process according to one embodiment of the present invention.

BRIEF DESCRIPTION OF MAIN SYMBOLS
AND NUMERALS USED IN DRAWINGS

| | |
|---|---|
| 1: adsorption chamber | 2: rotary valve |
| 3: raffinate column | 4: final extraction column |
| 5: circulation pump | 11: bed |
| 12: grid | 13: bed line |
| 14: center pipe | 21: multiple access line |
| 22: fluid mixture inlet port | 23: raffinate outlet port |
| 24: desorbent inlet port | 25: extract outlet port |
| 31: first separator | 41: second separator |

DETAILED DESCRIPTION OF THE INVENTION

According to the present invention, provided is a simulated moving bed adsorptive separation process, using a device for the simulated moving bed adsorptive separation process which comprises: an adsorption chamber for pretreatment which comprises a plurality of beds each bed containing a grid which is filled with adsorbent; a rotary valve for pretreatment which connects the adsorption chamber for pretreatment, a fluid mixture inlet port, a raffinate outlet port, a desorbent inlet port and a pretreated extract outlet port to a multiple access line; a pretreated extract column for separating the pretreated extract from the pretreated extract outlet port, turning back one of the separated fractions to the adsorption chamber for pretreatment and feeding the rest of the separated fractions to a main adsorption chamber as a pretreated fluid mixture; a main adsorption chamber which comprises a plurality of beds each bed containing a grid which is filled with adsorbent; at least one main rotary valve which connects the plurality of adsorption chambers, a pretreated fluid mixture inlet port, a raffinate outlet port, a desorbent inlet port and an extract outlet port to the multiple access line; a raffinate column for separating the raffinate from the raffinate outlet port, and turning back one of the separated fractions to the adsorption chamber for pretreatment and the main adsorption chamber; and a main extract column for separating the main extract from the extract outlet port, and turning back one of the separated fractions to the adsorption chamber for pretreatment and the main adsorption chamber, wherein the fluid mixture inlet port, the raffinate outlet port, the extract outlet port and the desorbent inlet port are moved to be connected to the adjacent multiple access line, by means of the rotation of the rotary valve at switching time, and comprising the steps of:
(a) contacting the fluid mixture with a solid adsorbent in the adsorption chamber for pretreatment and desorbing it with a desorbent so as to prepare a pretreated extract Which comprises the desorbent and at least one component from the fluid mixture, and flowing the pretreated extract to a pretreated extract column;

(b) separating the pretreated extract into a desorbent fraction which comprises mainly a desorbent and a pretreated fluid mixture fraction which comprises mainly at least one component from the fluid mixture in the pretreated extract column, and turning the desorbent fraction to the adsorption chamber for pretreatment;

(c) contacting the pretreated fluid mixture with a solid adsorbent in the main adsorption chamber and desorbing it with a desorbent so as to prepare the main extract which comprises the desorbent and at least one component from the fluid mixture, and flowing the main extract to the main extract column; and (d) separating the main extract into a desorbent fraction which comprises mainly the desorbent and the final product fraction which comprises mainly at least one component of the fluid mixture in the main extract column, and turning back the desorbent fraction to the adsorption chamber for pretreatment and the main adsorption chamber.

According to the simulated moving bed adsorptive separation process of the present invention, the pretreated fluid mixture fraction obtained from the pretreated extract column can be directly fed to the main adsorption chamber or optionally can be transferred to a separate reservoir for future use.

Further, according to the simulated moving bed adsorptive separation process of the present invention, the final product fraction also can be recovered by the separation using a crystallizer.

Still further, according to the present invention, provided is a device for the simulated moving bed adsorptive separation process comprising:

an adsorption chamber for pretreatment which comprises a plurality of beds each bed containing a grid which is filled with adsorbent;

a rotary valve for pretreatment which connects the adsorption chamber for pretreatment, a fluid mixture inlet port, a raffinate outlet port, a desorbent inlet port and a pretreated extract outlet port to a multiple access line;

a pretreated extract column for separating the pretreated extract from the pretreated extract outlet port, turning back one of the separated fractions to the adsorption chamber for pretreatment and feeding the rest of the separated fractions to a main adsorption chamber as a pretreated fluid mixture;

a main adsorption chamber which comprises a plurality of beds each bed containing a grid which is filled with adsorbent;

at least one main rotary valve which connects the plurality of adsorption chambers, a pretreated fluid mixture inlet port, a raffinate outlet port, a desorbent inlet port and an extract outlet port to the multiple access line;

a raffinate column for separating the raffinate from the raffinate outlet port, and turning back one of the separated fractions to the adsorption chamber for pretreatment and the main adsorption chamber; and a main extract column for separating the main extract from the extract outlet port, and turning back one of the separated fractions to the adsorption chamber for pretreatment and the main adsorption chamber, wherein the fluid mixture inlet port, the raffinate outlet port, the extract outlet port and the desorbent inlet port are moved to be connected to the adjacent multiple access line, by means of the rotation of the rotary valve at switching time.

According to the device for a simulated moving bed adsorptive separation process of the present invention, the pretreated extract column can be directly connected to the pretreated fluid mixture inlet port in order to immediately transfer the pretreated fluid mixture fraction separated by the pretreated extract column to the main adsorption chamber, or optionally the pretreated extract column can be connected to a separate reservoir for keeping the pretreated fluid mixture fraction in order to transfer the pretreated fluid mixture fraction to the reservoir for future use.

Further, the SMB adsorptive separation device according to the present invention may further comprise a crystallizer to obtain the final product.

Hereinafter, the present invention is further described in detail with the reference of the drawings attached to this specification.

Figure 4:
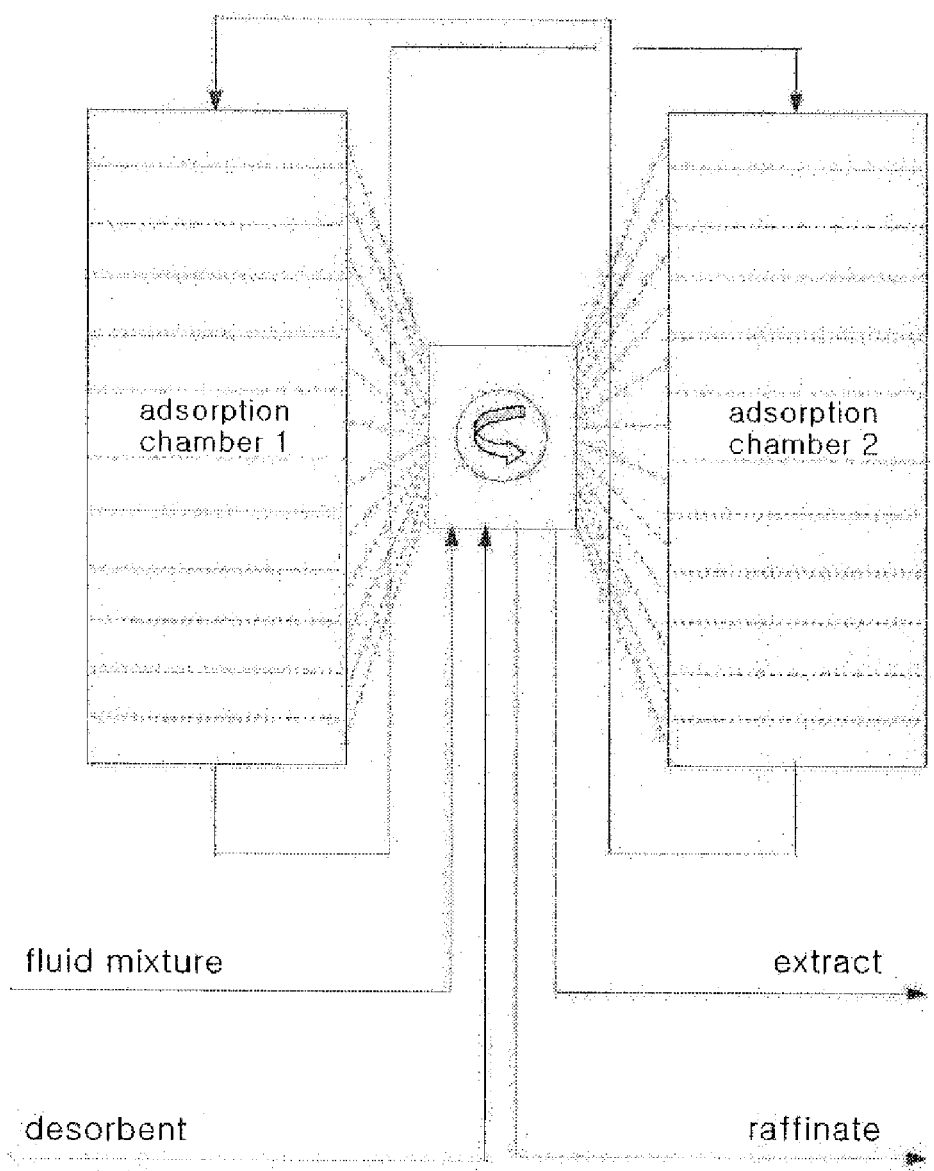
FIG. 4 is a schematic view of one embodiment of a conventional simulated moving adsorptive separation device which uses two adsorption chambers at the same time.

Each of FIGS. 1 and 4 is a schematic view illustrating one embodiment of a device used in conventional SMB separation process.

In the SMB adsorptive separation devices illustrated in FIGS. 1 and 4, two adsorption chambers having multiple layers of beds are provided, wherein each bed is filled with adsorbent. Each bed in the adsorption chambers is connected to a rotary valve through a multiple access line. The number of beds is traditionally 12 per chamber, however it is not specifically restricted to this.

The rotary valve connects each of two inlet ports and two outlet ports including a fluid mixture inlet port, a raffinate outlet port, a desorbent inlet port and an extract outlet port to the multiple access line. The detailed structure of the rotary valve is known to and easily practiced by a person who has ordinary knowledge in this art.

The raffinate column 3 recovers the raffinate from the raffinate outlet port 22 by using a first separator, and turns a portion of the raffinate back to the desorbent inlet port 24 as a desorbent.

The extract column 4 recovers the extract from the extract outlet port 25 by using a second separator, and turns a portion of the extract back to the desorbent inlet port 24 as a desorbent.

In SMB adsorptive separation process, the flow of a stationery phase is not practically realized. Instead, positions of ports for desorbent, extract, fluid mixture (feed) and raffinate are moved in the direction of the flow of a mobile phase at a certain time interval of switching, to move the columns in the counter direction relative to the flow direction of the mobile phase, with each port as the center. As such, the virtual flow of the stationery phase can be made to simulate the counterflow to the flow of the mobile phase. The adsorbent used as a stationery phase is filled into the bed.

Although each position of ports 22,23,24,25 for desorbent, extract, fluid mixture feed) and raffinate cannot be continuously moved, similar effects can be obtained by providing multiple access line 21 and periodically moving each flow to adjacent line by using a rotary valve at a given time interval of switching time, as illustrated in FIGS. 1 and 4. During the process, a material with lower adsorption in the fluid feed mixture injected through a fluid feed inlet port comes out of a raffinate outlet port along the mobile phase, and a material with higher adsorption in the fluid feed mixture is adsorbed to each adsorbent bed 11 in the adsorbent chamber. As the column relatively moves at a certain switching time, the adsorbed material can be recovered through the extract outlet port 25 after a certain time elapse.

Figure 5:
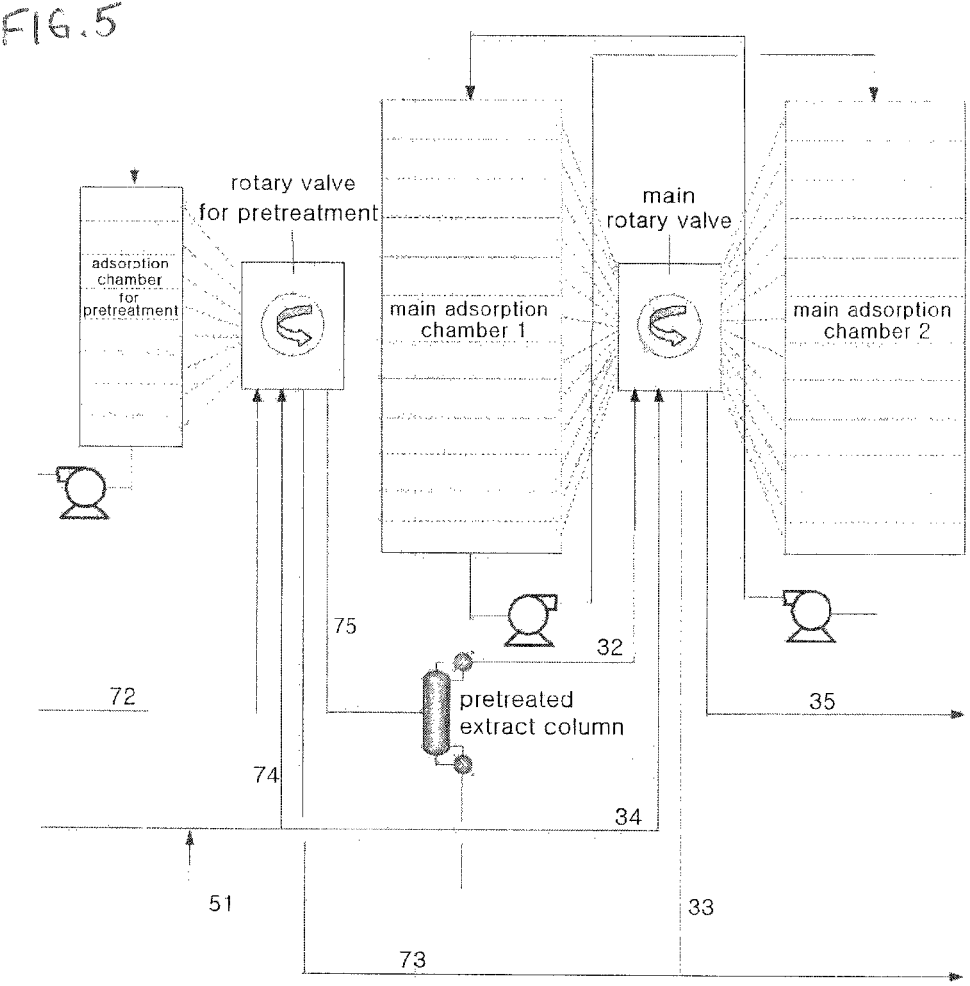
FIG. 5 is a schematic view of one embodiment of a simulated moving bed adsorptive separation device according to the present invention, which pretreats feed by using a single adsorption chamber.

FIG. 5 is a schematic view of a device for a SMB adsorptive separation process according to one embodiment of the present invention. As seen from FIG. 5, the device for a SMB adsorptive separation process according to one embodiment of the present invention, unlike the device shown in FIGS. 1 and 4, employs an adsorption chamber for pretreatment and two main adsorption chambers (a first adsorption chamber and a second adsorption chamber), wherein the adsorption chamber for pretreatment and two main adsorption chambers are connected to each rotary valve (a rotary valve for pretreatment and a main rotary valve) through multiple access line, and a column for a pretreated extract is placed between the rotary valve for pretreatment and the main rotary valve Another embodiment of a device used for a SMB adsorptive separation process according to the present invention may comprise two main adsorption chambers equipped continuously, by using two rotary valves. In this case, the pretreated fluid mixture obtained from the column for the pretreated extract, is fed to the first main adsorption chamber through the first rotary valve, and then the extract out of the first main adsorption chamber is, preferably separated from desorbent in a column, then fed to the second main adsorption chamber as a feed via the second rotary valve.

According to FIG. 5, in the device for a SMB adsorptive separation process according to the present invention, unlike the conventional Parex process, a fluid mixture 72, i.e. a feed, and a desorbent 74 are introduced into the adsorption chamber for pretreatment, then pretreated extract 75 and raffinate 73 come out of the adsorption chamber for pretreatment. The pretreated extract 75 is fed to the column for pretreated extract, in which the pretreated extract is separated as a desorbent fraction mainly comprising desorbent and a pretreated fluid mixture fraction which comprises mainly the components to be ultimately separated. The desorbent fraction 51 is turned back to the adsorption chamber for pretreatment, and the pretreated fluid mixture fraction 32 is transferred to the main rotary valve for being introduced into the two main adsorption chambers. Meanwhile, other parts of the process such as the introduction of a desorbent 34 into the main adsorption chamber and the discharging of the main extract 35 and raffinate 33 can be carried out as in the conventional Parex process.

Figure 2:
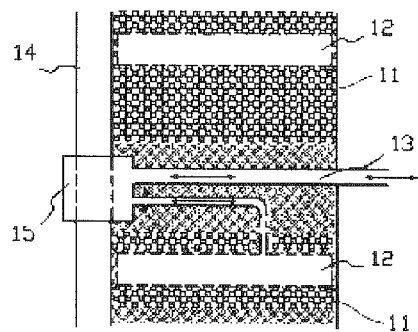
FIG. 2 is a magnified view of the part 11a of the device shown in FIG. 1, which is a schematic cross-sectional view of the bed in an adsorption chamber according to one embodiment of the present invention.
Figure 3:
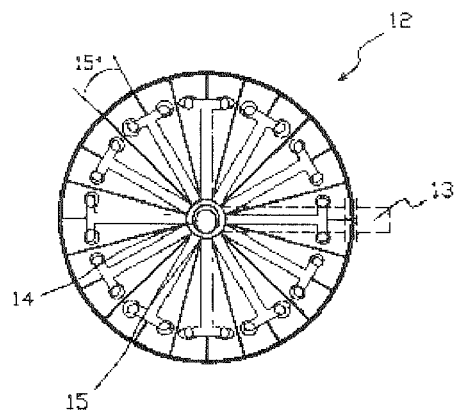
FIG. 3 is a plan view of a grid formed in the bed of an adsorption chamber in a device used for a simulated moving bed adsorptive separation process according to one embodiment of the present invention.

FIG. 2 is a magnified view of the part 11a illustrated in FIG. 1, which is a schematic cross-sectional view of a bed 11 in an adsorption chamber according to the present invention, and FIG. 3 is a plan view of a grid 12 formed in the bed 11 according to the present invention.

As illustrated in FIG. 2, the bed 11 comprises a space for supporting the adsorbent therein, i.e. grid 12. The movement of the fluid flow between the upper and the lower beds is achieved through the grid 12. The grid 12 is connected to a center pipe distributor 15, and then to the multiple access line 21 through a bed line 13. As shown in FIG. 3, the grid 12 of the present invention is formed of two layers of screen, and thus served as a separating wall of the bed 11 by allowing only fluid flow of liquid phase to pass through. The grid 12 is comprised of pie-shaped 24 pieces.

Figure 6:
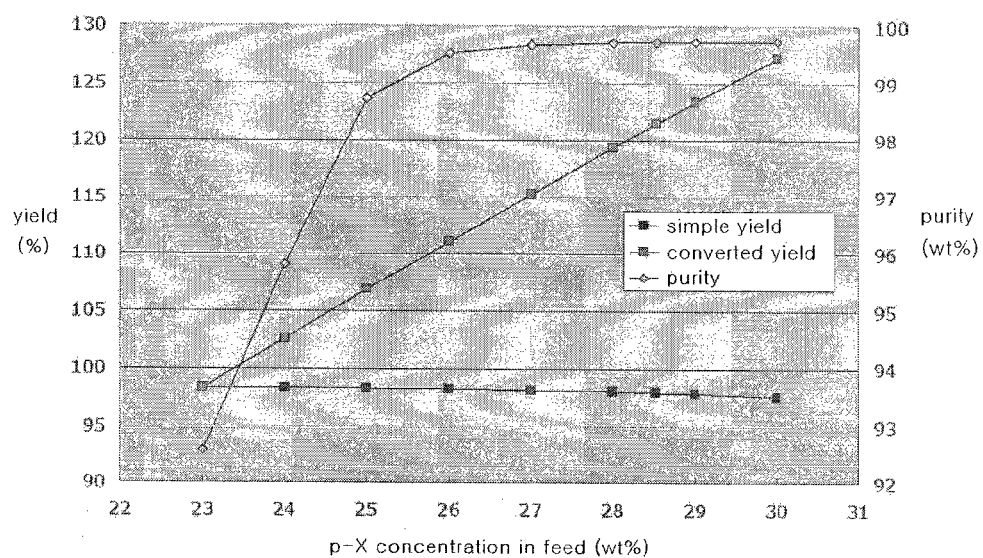
FIG. 6 is a plot which discloses the changes in productivity represented as the changes of the converted yield depending on the concentration of p-xylene in the feed, during the simulated moving bed adsorptive separation process for separating p-xylene.

As in the present invention, when the concentration of a component to be separated in a feed which is introduced to the main adsorption chamber is raised by using an adsorption chamber for pretreatment, the simple yield itself becomes rather reduced, however the converted yield becomes increased, resulting in the increase in productivity. The term, converted yield used herein refers to a value obtained by multiplying the simple yield by the concentration of the component to be separated in the feed, which is used as an indicator for substantial productivity. FIG. 6 is a plot which discloses the changes in productivity represented as changes of the converted yield depending on the concentration of p-xylene in the feed during the simulated moving bed adsorptive separation process for separating p-xylene. In FIG. 6, it should be noted that the converted yield can have the value of 100% or more, since it has been calculated based on a feed comprising 23 wt % of p-xylene.

The present invention is further described in detail through the following example. However, the scope of the present invention is by no means restricted or limited by the example which has only illustrative purpose.

EXAMPLE AND COMPARATIVE EXAMPLE

In this example, a process for adsorptive separation of p-xylene from an aromatic hydrocarbon mixture which comprises other types of xylene isomers was carried out by using a SMB adsorptive separation device as shown in FIG. 4, except the construction for increasing the concentration of p-xylene in the feed being introduced to the main adsorption chamber by using an adsorption chamber for pretreatment, a rotary valve for pretreatment and a column for pretreated extract as shown in FIG. 5 In the meantime, in a comparative example, the process was carried out by using the SMB adsorptive separation device as shown in FIG. 4, under the same process conditions as in the above example.

The concentration of p-xylene (PX) in the feed being introduced into the main adsorption chamber, simple yield of the final product obtained from the adsorptive separation of p-xylene, purity of the final product, and converted yield are summarized in Table 1 below.

TABLE 1

| | PX concentration in a feed (wt %) | Simple yield (%) | Purity (wt %) | Converted yield (%) |
|---|---|---|---|---|
| Example | 36 | 95.1 | 99.7 | 148 |
| Comparative Example | 23.5 | 98.5 | 99.7 | 100 (base) |

As it is shown in Table 1, according to the example of the present invention, in which the concentration of p-xylene in the feed being introduced into the main adsorption chamber was increased, the concentration of p-xylene in the feed was increased by 50% or more as compared to the conventional process which does not include the pretreatment of a feed, and in result, it can be found that the whole productivity was remarkably improved, although simple yield of the final product was rather reduced little bit.

INDUSTRIAL AVAILABILITY

As it has been described so far, the present invention makes possible to significantly improve productivity of the final product in a SMB adsorptive separation process, while maintaining the purity of the final product to an appropriate level.

What is claimed is:

1. A simulated moving bed adsorptive separation process, using a device for the simulated moving bed adsorptive separation process which comprises: an adsorption chamber for pretreatment which comprises a plurality of beds each bed containing a grid which is filled with adsorbent; a rotary valve for pretreatment which connects the adsorption chamber for pretreatment, a fluid mixture inlet port, a raffinate outlet port, a desorbent inlet port and a pretreated extract outlet port to a multiple access line; a pretreated extract column for separating the pretreated extract from the pretreated extract outlet port, turning back one of the separated fractions to the adsorption chamber for pretreatment and feeding the rest of the separated fractions to a main adsorption chamber as a pretreated fluid mixture; a main adsorption chamber which comprises a plurality of beds each bed containing a grid which is filled with adsorbent; at least one main rotary valve which connects the plurality of adsorption chambers, a pretreated fluid mixture inlet port, a raffinate outlet port, a desorbent inlet port and an extract outlet port to the multiple access line; a raffinate column for separating the raffinate from the raffinate outlet port, and turning back one of the separated fractions to the adsorption chamber for pretreatment and the main adsorption chamber; and a main extract column for separating the main extract from the extract outlet port, and turning back one of the separated fractions to the adsorption chamber for pretreatment and the main adsorption chamber, wherein the fluid mixture inlet port, the raffinate outlet port, the extract outlet port and the desorbent inlet port are moved to be connected to the adjacent multiple access line, by means of the rotation of the rotary valve at switching time, and comprising the steps of:

(a) contacting the fluid mixture with a solid adsorbent in the adsorption chamber for pretreatment and desorbing it with a desorbent so as to prepare a pretreated extract which comprises the desorbent and at least one component from the fluid mixture, and flowing the pretreated extract to a pretreated extract column;

(b) separating the pretreated extract into a desorbent fraction which comprises mainly a desorbent and a pretreated fluid mixture fraction which comprises mainly at least one component from the fluid mixture in the pretreated extract column, and turning the desorbent fraction to the adsorption chamber for pretreatment;

(c) contacting the pretreated fluid mixture with a solid adsorbent in the main adsorption chamber and desorbing it with a desorbent so as to prepare the main extract which comprises the desorbent and at least one component from the fluid mixture, and flowing the main extract to the main extract column; and (d) separating the main extract into a desorbent fraction which comprises mainly the desorbent and the final product fraction which comprises mainly at least one component of the fluid mixture in the main extract column, and turning back the desorbent fraction to the adsorption chamber for pretreatment and the main adsorption chamber.

2. The simulated moving bed adsorptive separation process according to claim 1, wherein the pretreated fluid mixture fraction separated by the pretreated extract column is directly fed to the main adsorption chamber.

3. The simulated moving bed adsorptive separation process according to claim 1, wherein the pretreated fluid mixture fraction separated by the pretreated extract column is transferred to a separate reservoir.

4. The simulated moving bed adsorptive separation process according to claim 1, wherein a crystallizer is used for obtaining the final product.

5. A device for a simulated moving bed adsorptive separation process comprising:

an adsorption chamber for pretreatment which comprises a plurality of beds each bed containing a grid which is filled with adsorbent;

a rotary valve for pretreatment which connects the adsorption chamber for pretreatment, a fluid mixture inlet port, a raffinate outlet port, a desorbent inlet port and a pretreated extract outlet port to a multiple access line;

a pretreated extract column for separating the pretreated extract from the pretreated extract outlet port, turning back one of the separated fractions to the adsorption chamber for pretreatment and feeding the rest of the separated fractions to a main adsorption chamber as a pretreated fluid mixture;

a main adsorption chamber which comprises a plurality of beds each bed containing a grid which is filled with adsorbent;

at least one main rotary valve which connects the plurality of adsorption chambers, a pretreated fluid mixture inlet port, a raffinate outlet port, a desorbent inlet port and an extract outlet port to the multiple access line;

a raffinate column for separating the raffinate from the raffinate outlet port, and turning back one of the separated fractions to the adsorption chamber for pretreatment and the main adsorption chamber; and a main extract column for separating the main extract from the extract outlet port, and turning back one of the separated fractions to the adsorption chamber for pretreatment and the main adsorption chamber, wherein the fluid mixture inlet port, the raffinate outlet port, the extract outlet port and the desorbent inlet port are moved to be connected to the adjacent multiple access line, by means of the rotation of the rotary valve at switching time.

6. The device for the simulated moving bed adsorptive separation process according to claim 5, wherein the pretreated extract column is directly connected to the pretreated fluid mixture inlet port.

7. The device for the simulated moving bed adsorptive separation process according to claim 5, wherein the pretreated extract column is connected to a reservoir for keeping the pretreated fluid mixture fraction.

8. The device for the simulated moving bed adsorptive separation process according to claim 5, further comprising a crystallizer for obtaining the final product.

* * * * *